(12) United States Patent
Landesberg

(10) Patent No.: US 12,350,498 B2
(45) Date of Patent: Jul. 8, 2025

(54) TREATMENT OF CARDIAC DECOMPENSATION, PULMONARY CONGESTION AND DYSPNEA

(71) Applicant: Amir Landesberg, Haifa (IL)

(72) Inventor: Amir Landesberg, Haifa (IL)

(73) Assignee: Levron Cardiovascular Ltd., Yokneam Ilit (IL)

( * ) Notice: Subject to any disclaimer, the term of this patent is extended or adjusted under 35 U.S.C. 154(b) by 327 days.

(21) Appl. No.: 17/794,970

(22) PCT Filed: Jan. 28, 2021

(86) PCT No.: PCT/IB2021/050680
§ 371 (c)(1),
(2) Date: Jul. 24, 2022

(87) PCT Pub. No.: WO2021/152506
PCT Pub. Date: Aug. 5, 2021

(65) Prior Publication Data
US 2023/0077507 A1 Mar. 16, 2023

Related U.S. Application Data

(60) Provisional application No. 62/967,155, filed on Jan. 29, 2020.

(51) Int. Cl.
*A61N 1/365* (2006.01)

(52) U.S. Cl.
CPC .................. *A61N 1/36585* (2013.01)

(58) Field of Classification Search
None
See application file for complete search history.

(56) References Cited

U.S. PATENT DOCUMENTS

| | | |
|---|---|---|
| 4,155,356 A | 5/1979 | Venegas |
| 2008/0071317 A1 | 3/2008 | Stahmann et al. |
| 2011/0098583 A1 | 4/2011 | Pandia et al. |
| 2013/0006318 A1 | 1/2013 | Weiss et al. |
| 2013/0274821 A1 | 10/2013 | Hopper et al. |

OTHER PUBLICATIONS

PCT Search Report and Written Opinion PCT/IB2021/050680, May 25, 2021.

*Primary Examiner* — Paula J Stice
(74) *Attorney, Agent, or Firm* — Dekel Patent Ltd.; David Klein

(57) ABSTRACT

A method for treatment of cardiac problems includes performing modulation of a cardiac rhythm of a patient by increasing a number of heart beats the patient during time interval with high pleural pressure relative to the number during low (negative) pleural pressure, wherein an amplitude of the modulation of the cardiac rhythm between these segments is determined by severity of a respiratory effort and lung congestion of the patient.

21 Claims, 3 Drawing Sheets

TREATMENT OF CARDIAC DECOMPENSATION, PULMONARY CONGESTION AND DYSPNEA

FIELD OF THE INVENTION

The invention relates to a novel method and device for treatment of heart-failure and pulmonary congestion and also to prevention of atrial fibrillation; without limitation, the invention may be used for treatment of cardiac decompensation, amelioration of dyspnea and prevention of deterioration to pulmonary congestion and pulmonary edema. It applies to patients with acute or chronic heart failure from any etiology.

BACKGROUND OF THE INVENTION

Heart failure is a leading pandemic that is associated with poor quality of life, high morbidity and mortality. There are various treatments for heart failure: various drugs, resynchronization of the myocardial contraction by pacing the heart at different sites (CRT, cardiac resynchronization therapy), cardiac contractility modulation, neurohumoral stimulation, mechanical assist devices, attempts to use stem-cell therapy for myocardial regeneration and utilization of various materials for tissue rejuvenation. Despite the significant advances in all the suggested technologies and therapies the mortality and morbidity are still high and quality of life is very poor. Moreover, the prevalence of heart failure is expected to grow in the near future with the aging of the population.

The main problem of all known solutions for the treatment of heart failure is that their effectiveness is very limited. The current solutions have only limited success in altering the course of the disease, although they may ameliorate of rate of heart failure progression. Few thousands of assist devices are implanted every year in patients with end-stage heart-failure. Although this technology significantly prolongs their survival, these patients are only a small fraction of the population that suffer from severe heart-failure, few thousands out of a population of more than 1.5 million patients with stage III-IV heart failure, in the USA alone. Moreover, the assist device technology is associated with high rate of complications as gastrointestinal bleeding, stroke, and right-heart failure. In addition, it is a very expensive technology.

Cardiac Resynchronization Therapy (CRT) is another advanced technology, but it is effective in only a small fraction of the patients with severe systolic heart failure (patients with ejection fraction below 35% and markedly prolonged QRS). Interestingly, more than half of the heart failure patients suffer from diastolic heart-failure, a problem in the filling of the left ventricle. The mechanisms underlying this type of heart failure are not well-understood and there is no effective remedy to this type of heart failure. This group of diastolic heart failure (or heart failure with preserved ejection fraction) is steadily growing with the aging of the population. Therefore, there is a crucial unmet need to develop novel technologies for the treatment of heart failure.

Three main paradigms have been suggested to explain the development of heart failure: (1) cardio-renal and volume overload, (2) cardio-circulation and coupling the cardiac function with the peripheral impedance, (3) neuro-humoral and the activation of the sympathetic system. The current available drug therapies and the various technologies relate to these three paradigms.

SUMMARY

The present invention provides novel methods and devices for treatment of heart-failure and pulmonary congestion and also to prevention of atrial fibrillation; without limitation, the invention may be used for treatment of cardiac decompensation, amelioration of dyspnea and prevention of deterioration to pulmonary congestion and pulmonary edema.

The invention can be used to treat the deterioration of heart failure, denoted as the "cardiopulmonary vicious cycle". The most cardinal complaint of severe heart failure and the main cause for rehospitalization is severe dyspnea. The inventor has found that the respiratory effort and the associated sensation of dyspnea are not only hallmarks of cardiac decompensation but the respiratory effort plays a pivotal role in the 'cardiopulmonary vicious cycle' that can lead to progressive deterioration.

The novel treatment is a breakthrough in the management of heart failure for the following main reasons:

1. It is based on a novel paradigm for understanding the deterioration of heart failure.
2. It counteracts the normal physiological control of cardiac pacing.
3. It is independent of the various etiologies of heart failure, and can treat all of them.
4. It provides assessment of the severity of cardiac decompensation and immediately provides a treatment that is proportional to the severity of the decompensation.
5. It can detect early deterioration and provide treatment before the patient may become symptomatic—provides personalized medicine with early detection and prevention.

Advantages of the invention include, without limitation:

1. It applies to the huge market of heart failure, and can be used in all the patients with stage 3 and 4 heart failure.
2. It applies to all forms of heart failure, independently of the etiology, whether it is heart failure with reduced ejection fraction or preserved ejection fraction.
3. It provides immediate treatment to the detected development of dyspnea or an increase in the intrapulmonary blood pressure (hemodynamic congestion).
4. It can detect the slow progression of the disease and treat it before the patients become symptomatic. Thus it provides prevention and can decrease the rate of hospitalization.
5. It represents novel autonomic control (diagnosis and treatment) of the human autonomic cardiac system. It enables tight continuous surveillance of the heart-failure patients, with tight monitoring of the changes in the hemodynamic congestion and the effectiveness of the treatment.
6. It is simple to implement. It is based on integration of pacing technology with sensing the respiratory effort and a novel algorithm.
7. It requires low power because it utilizes the power of the "respiratory pump" and the cardiac contraction to push blood out of the lung and to alleviate the hemodynamic congestion.
8. The expected adverse effects are low. The adverse effects may relate to the presence of a pacing electrode within the heart and to the modulation of the heart rate, and both have well-known low rate of adverse effects. Modulation of the heart rate is not expected to have any adverse effect, since patients with atrial fibrillation with rate control has the same prognosis as patients with tight rhythm control.

There is provided in accordance with a non-limiting embodiment of the invention method for treatment of cardiac problems, including performing modulation of a cardiac rhythm of a patient by increasing a number of heart beats during time segments with high pleural pressure relative to a number of heart beats in other time segments with relatively lower pleural pressure, wherein an amplitude of the modulation of the cardiac rhythm is determined by severity of a respiratory effort and lung congestion of the patient. The high pleural pressure is closer to zero than the relatively lower pleural pressure.

The method may further use the modulation of the cardiac pacing to remove fluids from a lung of the patient, to reduce pressures within pulmonary vessels of the patient and thereby reducing the respiratory effort and the sensation of dyspnea.

The method may further use the modulation of the cardiac pacing to reduce resistance to blood flow within pulmonary circulation of the patient and reducing the respiratory effort and thereby alleviating both right and left ventricle workloads.

The modulation of the cardiac pacing may further include sensors within a pleural space or/and intrathoracic vessels and/or heart chamber or/and a surface of a thorax and an epigastrium of the patient, that record and measure respiratory waves, and wherein severity of the respiratory effort is defined as peak to peak amplitude of the respiratory wave.

The modulation of the cardiac pacing may further include using a long-term central control system, with memory and communication units, that records past history of heart rate, respiratory dynamics and hemodynamic indices.

The modulation of the cardiac pacing may further include using a long-term central control system, with a central processing unit that analyzes the changes in hemodynamic congestion or hemodynamic pressure, respiratory effort and/or heart rates.

The modulation of the cardiac pacing may further include using a long-term central control system that sets a threshold level for segmentation of the respiratory cycles into intervals with relatively high pleural pressure and relatively low pleural pressure.

The modulation of the cardiac pacing may further include suppressing normal sinus node pacing.

The modulation of the cardiac pacing may further include an intentional increase in the number of heart beats during time intervals with high pleural pressure that suppresses sinus node pacing during the relatively low pressure time intervals by an autonomic nerve system of the patient, in response to a transient increase in cardiac output during the time interval with high pleural pressure.

The modulation of the cardiac pacing may further include an algorithm of adaptive control of the modulation, within a long-term control system, using feedback from sensors that assess respiratory effort level, to control the modulation of the cardiac pacing, wherein the control of the moculation includes determining a number of pacing beats that should be added per minutes (NpM), that are added during the high pleural pressure intervals, and wherein a depth of the modulation (NpM) increases with severity of the monitored respiratory effort.

The method may further include using a long-term central control system that determines a respiratory rate (RR) interval of elicited pacing, based on past history of electrocardiogram (ECG) recordings.

The method may further include using a real time control unit that accepts a threshold for segmentation of the respiratory wave, the required number of additional pacing (NpM) and the RR interval of the elicited pacing, and identifies in real time the beginning of each high pleural pressure interval and computes the pacing time based on identifying the last heartbeat, the number of pacing provided recently and the required NpM.

The method may further include using a real time control unit and an output power unit that executes the real time additional pacing.

The modulation of the cardiac pacing may be carried out by pacing electrodes placed within at least one of the cardiac chambers.

BRIEF DESCRIPTION OF THE DRAWINGS

The present invention will be understood and appreciated more fully from the following detailed description taken in conjunction with the drawings in which.

DETAILED DESCRIPTION

Figure 1:
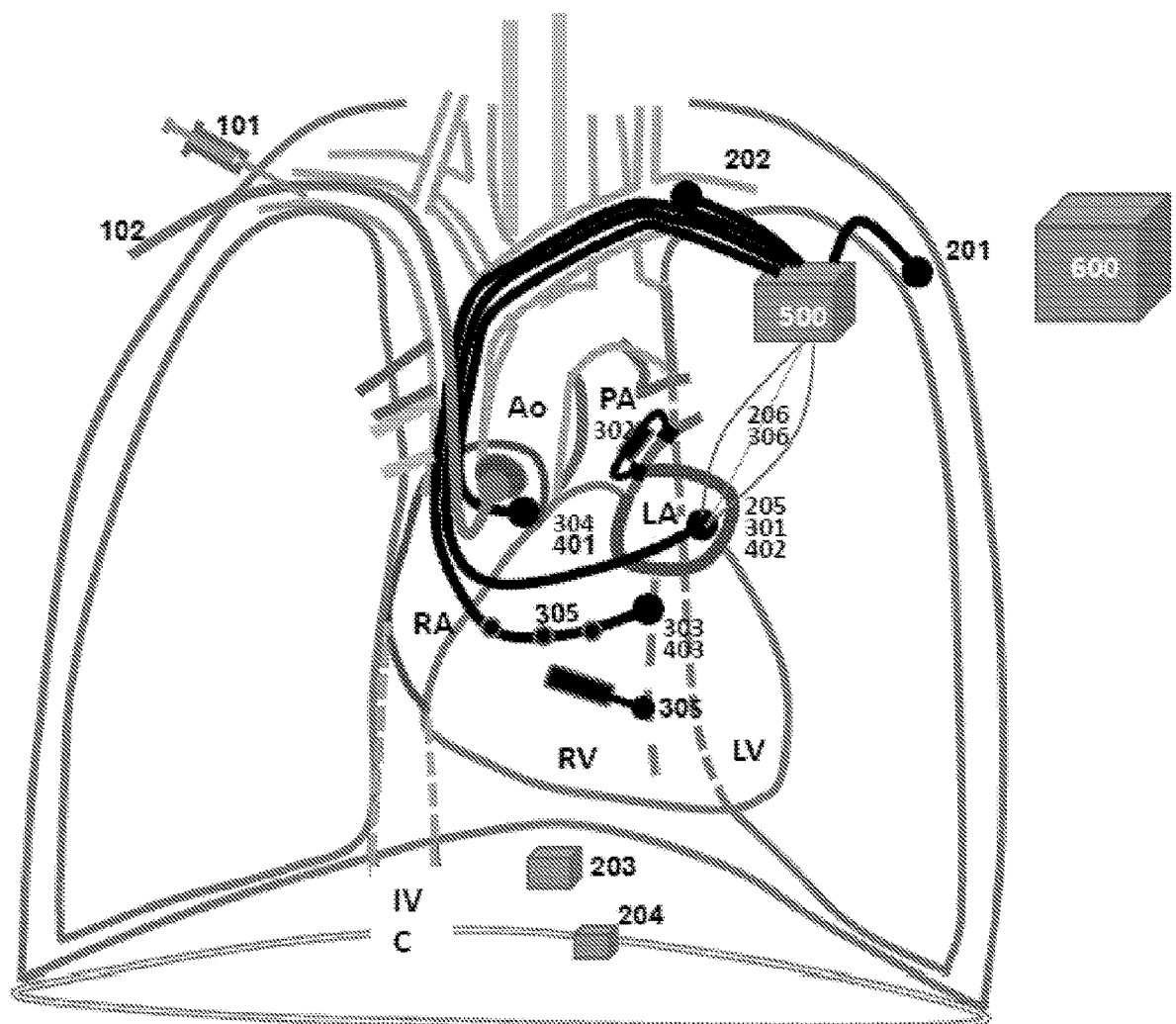
FIG. 1 is a simplified illustration of embodiments of the novel cardiopulmonary reverse cycling therapy (CPRS) of the invention. It is called "cardiopulmonary reverse cycling" since it breaks the "cardiopulmonary vicious cycle" and reverses the various interactions that causes progressive deterioration.

The invention provides a novel cardiopulmonary reverse cycling therapy for treating what is called herein the "cardiopulmonary vicious cycle", described herein. No prior art has related to the crucial role of the respiratory effort in the development of cardiac decompensation.

The novel "cardiopulmonary reverse cycling" (CPRC) aims to: 1. break all the cardiopulmonary vicious feedback loops that lead to cardiac decompensation, 2. prevent the development of hemodynamic and pulmonary congestions by utilizing the large changes in the intrathoracic pressure (the work of the respiratory pump/machine) to pull blood and fluid out of the lung back into the peripheral circulation, 3. decrease the transmural pressure across the pulmonary capillaries and the left atrium, and thereby to improve lung compliance. 4. ameliorate the problem of dyspnea, and 5. Decrease the workloads of both the right and left ventricles. The "cardiopulmonary vicious cycle" leads to progressive increase in the pulmonary capillary pressure and lung congestion and increase the workloads of the two heart ventricles. The device provides cardiopulmonary reverse cycling by reversing these ominous effects of the vicious cycle.

The device utilizes the works that are generated by the respiratory system (the "respiratory pump") and cardiac contractions in order to remove fluids from the lung, to reduce the pressures within the pulmonary vessels and to reduce the resistance to blood flow within the pulmonary circulation. These effects alleviate the hemodynamic and lung congestions. The pressures in the pulmonary circulation (hemodynamic congestion) and the amount of blood and fluids with the lung (lung congestion) are mainly determined by the inflow of blood into the lung through the right ventricle and the outflow of blood out from the lung back into the peripheral circulation through the left ventricle. However, these inflow and outflow, through the right and left ventricle, are modulated by the intrathoracic pressure. In the presence of a deep negative intrathoracic pressure the inflow into the lung is larger than the outflow from the lung. The opposite occurs in the presence of close to zero and positive intrathoracic pressure. Therefore, the inflow and outflow are modulated by the respiratory pump. The device utilized the pressures that are generated by the respiratory pump to shift blood out of the lung and to reduce the pressures in the pulmonary circulation. It is done by pacing the heart and increasing the number of heart beats when the intrathoracic pressure is close to zero relative to the number during deep negative intrathoracic pressure.

The anticipated pacing rate is very low, about a single paced beat every 100 normal heart beats. The mean cardiac stroke volume of an adult is about 70 ml. Let assume that each pacing during the appropriate time interval (close to zero intrathoracic pressure) shift only 0.2 ml of blood out of the lung (0.3% of the stroke volume), i.e. the stroke volumes of the right and left ventricles are 69.9 ml and 70.1 ml, respectively. Thus, to shift a relative large amount of 200 ml of blood out of the lung we have to add 1000 heat beats at the appropriate time window. However, in a single day we have on average about 20,000 breath cycle and 100,000 heart beats. Thus, only a modest pacing of once every 20 breath cycle or 100 heart beats is needed. Moreover, it was well established the cardiac decompensation of chronic heart failure patient develops and progress slowly over a period of 2 to 3 weeks. Thus there is reverse cycling can be extended over couple of days.

It is important to note that the device has insignificant effect on the heart rate (less than 1%), in contrast to other patents (%%%%) that aims to change the heart rate according the breathing rate or phases.

It is important to note that the device does not directly change the breathing rate, as was suggested by various other patents (U.S. Pat. Nos. 8,509,902, 8,483,833, 9,149,642), on the contrary, it utilizes the respiratory pump to shift blood out of the lung. Moreover, in contract to these patents that suggest to pace the heart only when the patient is asleep, this device aims to work around the clock and also to alleviate the respiratory effort during physical activities.

Figure 4:
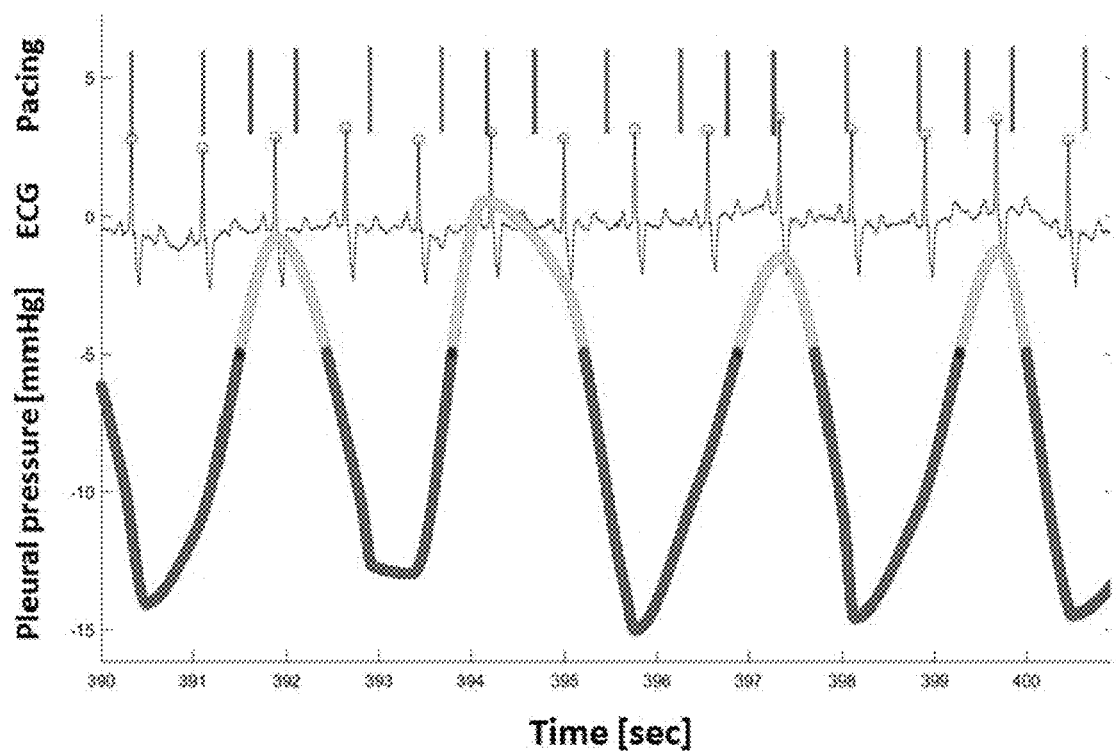
FIG. 4 depicts an example of the suggested synchronization of the cardiac pacing to the changes in the intrathoracic pressure and swings in the respiratory wave, based on data from heart failure patient. The upper bars denote the imposed pacing (red bars) over the native regular sinus pacing (blue bars) on top of the recorded ECG. The lower trace presents the measured changes in the intrathoracic pressure. Note the patient suffer from severe dyspnea with respiratory effort (peak to peak amplitude) of 15 mmHg, about 5 fold the normal respiratory effort. The novel algorithm sets a threshold (at −5 mmHg in this example) and segments the respiratory cycles into two types of time intervals: (1) Time intervals with deep negative intrathoracic pressure (red), at end inspiration and early expiration. (2) Time intervals with intrathoracic pressure close to zero (green). The system adds excitations when the intrathoracic pressure is close to zero (green), to provide cardiopulmonary reverse cycling and to reduce the hemodynamic and lung congestions.

Moreover, in contract to other patents, the pacing is not aligned to a simple segmentation of breathing cycle to inspiration and expiration phase, but based on the intrathoracic pressure levels, as depicted in FIG. 4. Inspiration is defined the time interval of inhalation, when the intrathoracic pressure drop from a pressure close to zero to the lowest negative intrathoracic pressure. Thus pacing during the inspiratory phase as suggested by other U.S. Pat. Nos. 8,509,902, 8,483,833) will not provide the anticipated cardiopulmonary reverse cycling, since pacing at low negative intrathoracic pressure only accentuates the vicious cycle and lung congestion. Similarly, pacing during the expiratory phase is ineffective, since the intrathoracic pressure is very low at the beginning of the expiration phase. The appropriate pacing widow cross the inspiration and expiration phases, and start before the end expiration and end after the beginning of inspiration. This segmentation of the respiratory cycle is unique to this embodiment, in comparison the all the other suggested pacing of the heart (U.S. Pat. Nos. 8,509, 902, 8,483,833).

Figure 2:
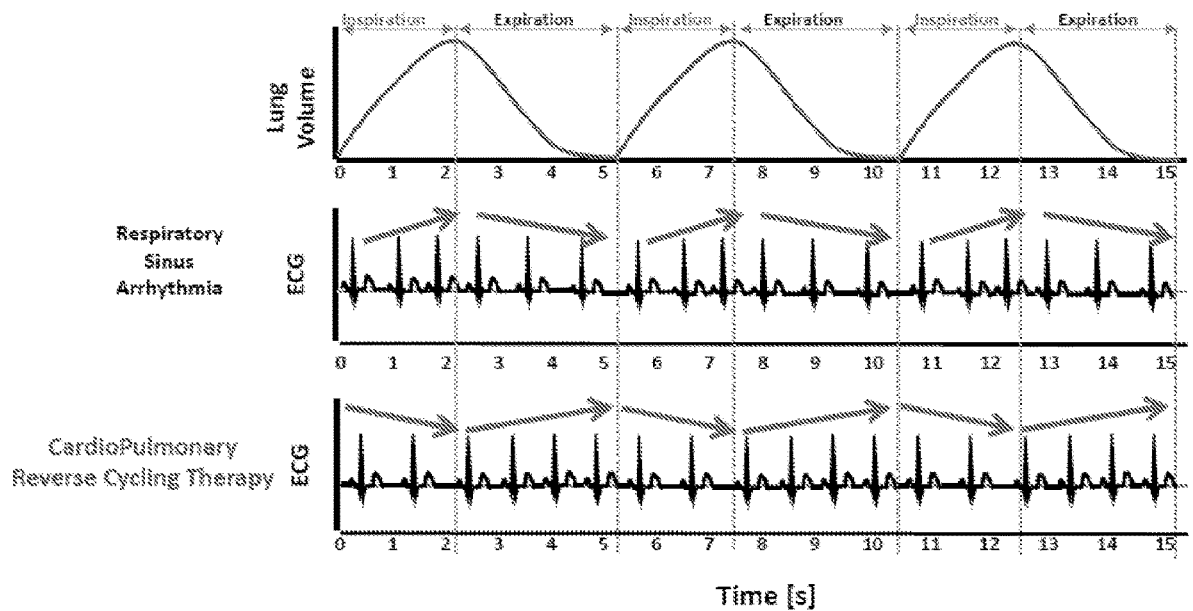
FIG. 2 is a simplified illustration of "respiratory sinus arrhythmia", which is a normal physiological increase in the heart rate during inspiration and decrease in the heart rate during expiration (depicted by the arrows). The cardiopulmonary reverse cycling therapy of the invention counteracts with the normal physiology and increases the heart rate only when the intrathoracic pressure is close to zero, at end expiration and the beginning of inspiration.

The invention surprisingly achieves this by using a counterintuitive mode of pacing the heart, which is opposite to the physiological autonomic modulation of the cardiac pacing by the respiration, which is denoted as "respiratory sinus arrhythmia". While in the physiological respiratory sinus arrhythmia the heart rate increases during inspiration, when the intrathoracic pressure drop down to the deepest negative pressure, the CPRC performs the opposite mode of pacing and increases the heart rate when the intrathoracic pressure is close to zero, as depicted in FIGS. 2 and 4. Moreover, the amplitude of the modulation of the cardiac pacing is determined by the severity of the respiratory effort and lung congestion.

The novel CPRC may include the following elements:

A. Means for suppressing the normal sinus node pacing, to decrease the normal pacing rate when the intrathoracic pressure is below the threshold. This may include at least one of the following:
 a. Simple utilization of drugs that decrease the heart rate (101 in FIG. 1), as beta-blocker or specific suppressor of the sinus node rhythm as ivabradine (inhibits the funny currents).
 b. Any invasive or minimally invasive way (102 in FIG. 1) to depress the sinus node activity.
 c. Selective addition of heart pacing only during time intervals where the intrathoracic pressure is above the threshold and close to zero. This mode by itself induces cardiopulmonary reverse cycling as explained above. Moreover, addition of cardiac pacing, amelioration of the symptom of dyspnea and decreasing the workloads of the heat downregulate the autonomic sympathetic nerve system, and decrease the normal sinus node rate.

B. Sensors that monitor the respiration and detect the inspiration and expiration phases, and can quantify the changes in the intrathoracic pressure:
 a. Pressure sensors that are inserted into the intrathoracic space (201 in FIG. 1).
 b. Sensors within any of the intrathoracic arterial or venous vessels (202 in FIG. 1), since the pressures within the blood vessels are modulated by the changes in the intrathoracic pressure. The heart and the great vessels are within the mediastinum and are surrounded by the intrathoracic pressure. The intrapulmonary vessels are connected to the great vessels in the mediastinum. Thus, breathing changes the intrathoracic pressure and affects the right and left ventricle functions and pressure, and it also modulates the pressure in the entire pulmonary circulation.
 c. Any sensor that monitors the chest wall motions and can detect the respiratory phases (203 in FIG. 1), including any belt (piezo, impedance, inductance, optical) that is used for monitoring the respiration (204 in FIG. 1).
 d. Sensors within the heart (e.g. right or/and left atrium) (205 in FIG. 1) since the pressures within the cardiac chambers, and especially within the right and left atria, are modulated by the changes in the intrathoracic pressure.
 e. Any impedance technology, between any intra or extra-thoracic electrodes or the main unit (206 in FIG. 1) that is used to quantify the changes in the impedance during the respiratory phases.
 f. Any analysis of respiratory induced changes in the electrocardiography (ECG), as monitoring the chest impedance through the ECG electrodes or monitoring the changes in the heart axis during the respiratory cycle.
 g. Any sensor that quantify the changes in the airflow, as thermistors, microphones vibrations accelerometers or stethoscopes.

C. Sensors that quantify the severity of the respiratory efforts. All the above sensors (201 to 206, a to g in the previous section) may be used to quantify the severity of the respiratory effort and dyspnea. The intrapleural sensors can measure the peak to peak amplitude of the changes in the intrathoracic pressure, and can differentiate between the severity of the inspiratory and expiratory efforts. Similarly, all the intravascular pressure sensors within the chest, can quantify the amplitude of the modulation in the intravascular pressure by the respiratory effort.

D. Sensors that quantify cardiac functions and the severity of heart failure, including:
 a. The pressure within the left-atrium (301 in FIG. 1)
 b. The pulmonary artery pressure (302 in FIG. 1)
 c. The pressure within the right ventricle (303 in FIG. 1), that provides the pulmonary artery pressure during the ejection phase and the right-ventricle end-diastolic pressure.
 d. The pressure within the right atrium (304 in FIG. 1) to assess the severity of right heart failure.
 e. Pressure within the left atria, utilizing transseptal catheter or sensor that is located within the left atria.
 e. Assessment of the changes in the cardiac output. The catheter within the right-ventricle (305 in FIG. 1) can be an impedance catheter that measures the right-ventricle volume and the stoke volume. This catheter can be used also to assessment of the cardiac output utilizing a thermodilution approach.
 f. Assessment of lung congestion by, for example, the impedance technology. Impedance may be measured between any intra or extra-thoracic electrodes and the central unit (306 in FIG. 1) or between any other set of intrathoracic electrodes.

E. The novel CPRC pacing may be modulated by the severity of the respiratory effort. If the patients feel well (low respiratory effort of about 3 mmHg), there is no need to impose the CPRC. As a more severe deterioration in the hemodynamic congestion is detected the device intensifies the pacing rate and increases the number of heart beat at time interval above the threshold (close to zero pleural pressure) and interval below the threshold (deep negative pleural pressure), as there is a more urgent need to reverse the effects of the cardiopulmonary vicious cycle. The severity of the respiratory effort can be assessed by all the above mentioned sensors (201 to 206).

F. Pacing Electrodes within the right or left atrium or/and ventricle. Pacing the left atrium or left ventricle is less often indicated.
 a. Pacing the right atrium (401 in FIG. 1) is the simplest mode. The CPRC pacing is elicited before the normal sinus beat (tRRew<tRRorg) and resets the sinus node. Atrial pacing is the preferred mode of pacing the heart in the absence of atrial arrhythmias as atrial fibrillation or conduction abnormalities, since it preserves the normal activation of the ventricles with a narrow QRS complex.
 b. Pacing the right-ventricle (402 in FIG. 1). In the presence of atrial fibrillations there is a need for direct pacing of the right ventricle. In the presence of atrioventricular block, the device can sense the right atrium and pace the right ventricle and set the appropriate AV-delay.
 c. The system can also use electrodes in the left side (left ventricle) to resynchronize the left ventricle function as in regular Cardiac Resynchronization Therapy (CRT).
 d. If the patient has an implanted Cardioversion device (ICD), the device can be integrated with the ICD and utilizes the ICD electros to pace the heart, or to used additional electrodes within the heart chambers.

Figure 5:
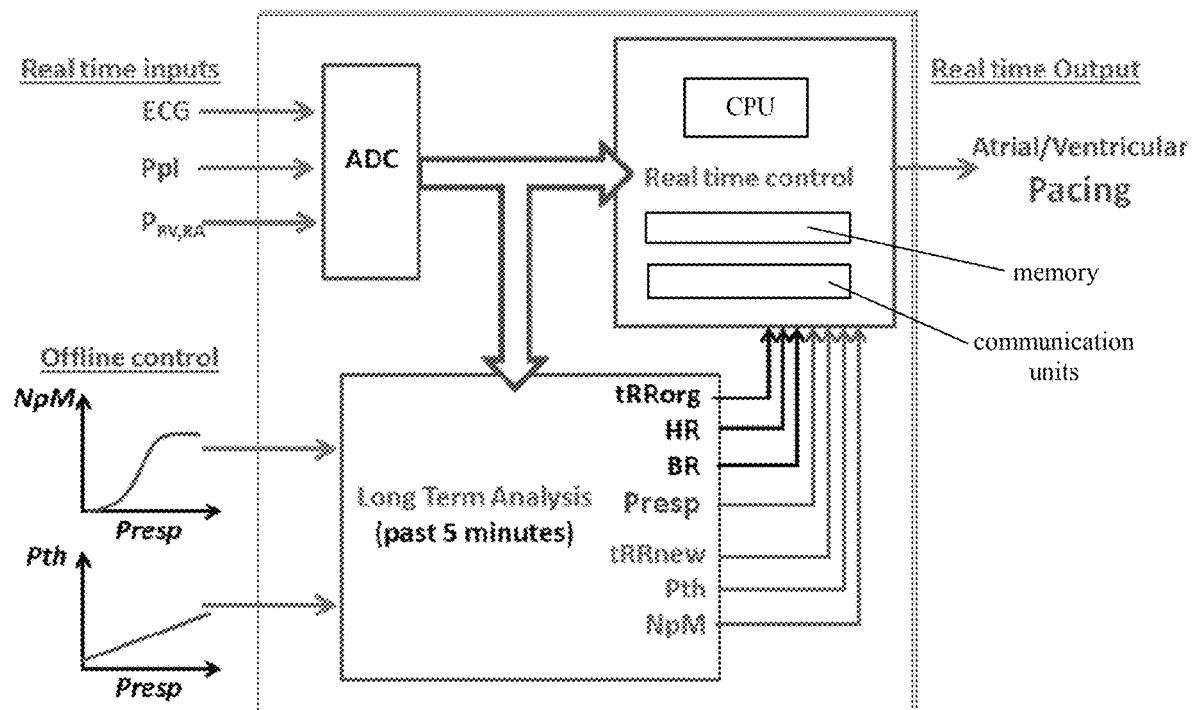
FIG. 5 presents schematics of the adaptive control of the excitation, that consists of two subsystems; one system analyzes long time intervals and analyzed the changes in the patient condition and the severity of dyspnea and heart failure (Long term analysis). The second system works at real time, and detects in real time the appropriate windows for excitation, and introduce the appropriate pacing (real time control). The inputs for the two subsystems are the ECG, direct measurement of intrathoracic pressure (Ppl, when measured directly) or the measured pressures by the various pressure transduces (Pra,Rv) among other possible measurements that are described in this embodiment. The long term analysis subsystem measures the mean heart rate (HR) and the associated normal mean RR internal (tRRorg), breathing rate (BR), and the mean respiratory effort. Based on these measurements and the recorded history of the patient, this system determines the following three parameters the determines the performance real-time control subsystem: (1) the RR interval of the pacing excitation (tRRnew, tRRnew<tRRorg), i.e. the time interval between the last normal heart beat and the paced beat. (2) The threshold level (Pth) that segment the respiratory cycle into time interval with deep negative pressure, where additional pacing should be avoided, and interval with close to zero intrathoracic pressure where pacing is allowed. (3) The number of additional pacing that should be introduced per minute (NpM). The latter determine the depth of the modulation. When the patient breath normally, and the respiratory effort is normal (about 3 mmHg), no pacing will be performed (NpM=0). As the respiratory effort increases the NpM should be raises, to provide the cardiopulmonary reverse cycling therapy.

G. Implantable main control units that controls the system (500 in FIG. 1). The implanted unit acquires the data, performs and novel algorithms, provides the novel CPRC pacing, records the patient condition, and communicates with the extra-corporal devices. The unit can be implanted under the pectoralis muscle as a regular pacemaker. The implantable unit include two subsystems, as depicted in FIG. 5. The long term control system provides the communication with the extra-corporal devices, record and store the data the patient electrical and various hemodynamics indices, determined the severity of dyspnea, and set the required parameter for the operation of the real control subsystem. The real control subsystem identifies the appropriate pacing widows based on the respiratory waves and the paces at the appropriate time following the last heart based on the designed RR interval. It is important to note that the pacing time cannot be predicted ahead of time as in most of the heart pacemakers since the pacing is synchronized to the respiratory wave and the respiratory wave is highly irregular with large instantaneous variation in the breathing rate, amplitude and shape.

H. The extra-corporal unit (600 in FIG. 1). The extra-corporal unit communicates with the implanted main unit and with the web if needed. The extra-corporal unit enables to set the various parameters of the implanted device, checks the appropriate functions of the various sensors and the thresholds of the various pacing electrodes. It can record the past history for the analysis of the various cardiac and respiratory events. The system provides a user-friendly interface for the medical-staff and enables remote surveillance by the medical-staff and experts in the field.

There are two physiological advantages for having the heart within the chest cage: The chest cage protects the heart and the main vessels from external trust and the "respiratory pump" increases the cardiac output by increasing the venous return. The normal physiological control of the heart rate aims to increase the cardiac output during exercises, and it is done efficiently in healthy subjects. An increase in the respiratory work by the "respiratory pump" (the diaphragm and all the respiratory and accessory muscles), decreases the intrathoracic pressure during inspiration and facilitates venous return to the right atrium. The cardiac output of the left ventricle is equal to the venous return, at steady state, and is limited by the venous return. Under normal physiological conditions, an increase in the venous return and the ensuing dilatation of the right atrium expedites the pacing rate of the sinus node. There is an increase in the heart rate especially during inspiration, since the venous return increases during inspiration. This phenomenon denoted is denoted as the 'respiratory sinus arrhythmia' and is depicted in FIG. 2. The increase in the cardiac output during exercise is due to an increase in the venous return to the heart and an increase in the heart rate.

However, except for this positive effect of the "respiratory pump" on the cardiac output under normal physiological condition, an increase in the respiratory effort has 5 severe detrimental effects on the pulmonary circulation and the cardiac workloads. The increase in the respiratory effort increases the: (1) intrapulmonary capillary pressure (PCWP). (2) pulmonary vascular resistance (PVR), pulmonary artery pressure (PAP) and right-ventricle afterload, (3) lung congestion by shifting blood into the lung, (4) LV afterload, and (5) metabolic demand due to the increase in the work of the respiratory muscles. All these mechanisms are described in more detailed in the attached supplement. These five adverse effects of an increase in the respiratory effort lead to accelerated decompensation in the presence of heart or lung diseases.

It is important to note that intrathoracic (pleural) pressure has significant effects on the pulmonary hemodynamics and lung congestion. Negative pleural pressure increases the lung blood pool and increases in the pulmonary bed pressure since it:

1. Decreases the transvascular diameters of the post-capillary pulmonary tree, leading to increase in the resistance to flow into the left atria and decrease in the outflow from the lung.

2. Increases the pulmonary vascular resistance in the entire pulmonary system and increases the pulmonary capillary and pulmonary artery pressures (relative to the instantaneous surrounding pleural pressure).

3. Increases the right atrial preload and the venous return to the right ventricle, which increases the right ventricle output.

4. Increases the afterload of the left ventricle and decrease the left-ventricle stroke volume. Thus, the inflow through the right ventricle increases while the outflow through the left ventricle decreases during inspiration. These effects accentuate with the increase in the respiratory effort.

All these effects are reversed when the pleural pressure is close to zero or above zero. During this phase there is:

1. An increase in the transvascular pressure in the post-capillary pulmonary tree, with a decrease in the resistance to flow from the lung into the left-atria, which increase the preload of the left-atria.

2. A decrease in the overall transpulmonary resistance, due to distension of the pulmonary blood vessels at higher pressure.

3. A decrease in the preload and venous return to the right-atria, and a decrease in the inflow of blood into the lung though the right ventricle.

4. A decrease in the LV afterload which augments the left-ventricle stroke volume. Thus, when the pleural pressure is negative the shift of blood from the periphery into the lung through the right ventricle increases. In contrast, close to zero pleural pressure is associated with an increase in the pulmonary vasculature diameter (lower resistance to flow through the pulmonary system) and a shift of blood out of the lung through the left ventricle.

Figure 3:
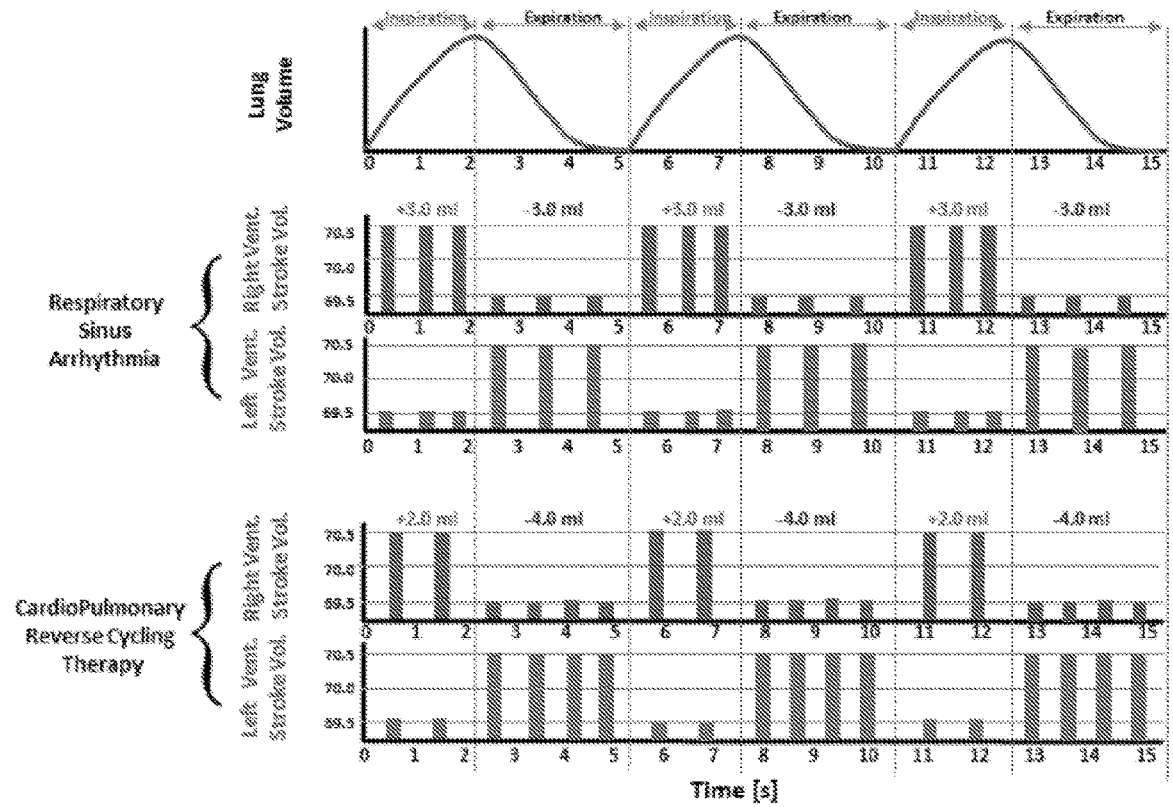
FIG. 3 is a simplified illustration that shows the effect of physiological respiratory sinus arrhythmia on lung congestion. During normal breathing there is an progressive increase in the heart rate and inflow into the lung during inspiration that is compensated by an increase in the outflow during expiration. In contrast the proposed cardiopulmonary reverse cycling therapy causes a net decrease in hemodynamic and lung congestions, by increasing the absolute number of cardiac contractions during time intervals with close to zero intrathoracic pressure over time interval with deep negative intrathoracic pressure.

Under steady state condition, the cardiac stroke volume is about 70 ml on average and about 70 ml of blood enters into the lung through the right-ventricle and the same amount of 70 ml is propelled out through the left ventricle, as schematically described in FIG. 4. However, when the pleural pressure dropped down the inflow though the right-ventricle increases, from 70 to 70.5 in the example in FIG. 3. At the same time, the outflow from the lung through the left ventricle decreases from 70.0 ml to 69.5 ml. When the pleural pressure is close to zero the picture is reversed, as shown the FIG. 4, and the amount of blood in the lung reaches a steady state. FIG. 3 also presents the physiological "respiratory sinus arrhythmia" where there is an increase in the heart rate during inspiration. The main strategy behind the present innovation is to utilize the "respiratory pump" (part of the inspiratory and expiratory works) and cardiac contractions in order to pump blood out of the lung and to alleviate the hemodynamic congestion. It is done by modulating cardiac pacing according to the changes in the pleural pressure, but counterintuitively, it works against the normal physiology and increases the heart rate during end expiration and early inspiration. During end inspiration and early expiration, when the pleural pressure is negative and the "respiratory pump" increases the right-ventricle preload and the left-ventricle afterload, the novel device decreases the pacing rate to reduce the net inflow into the lung. During late expiration and early inspiration, when the "respiratory pump" decreases the right-ventricle preload and increases the left-ventricle preload, the device increases the pacing rate to facilitate the removal of blood from the lung.

In the example presented in FIG. 3 the mean heart rate is 72 bpm during normal condition with respiratory sinus arrhythmia and cardiopulmonary reverse cycling therapy (CPRC). However, the device imposes higher pacing rate during late expiration and early inspiration phases, in contrast to the normal pacing. Consequently, during the two seconds of inspiration there are only two beats, while during the 3 seconds of expiration there are 4 beats. If there is an increase of 0.5 ml (+0.7% of the stroke volume) in the inflow to the lung and a decrease of 0.5 ml (−0.7%) in the outflow through the left-ventricle, for each heart beat during the negative pleural pressure intervals, each beat during this interval increases the lung blood volume by 1 ml of blood. In total, the decrease in the heart rate to two beats during the negative pressure interval decreases the shift of blood to only 2 ml (instead of 3) during this time interval. During the high pleural pressure intervals the picture is reversed, as described in FIG. 3. There is a decrease of 0.5 ml (−0.7% of the stroke volume) in the inflow to the lung and an increase of 0.5 ml (+0.7%) in the outflow through the left-ventricle, for each heartbeat. The CPRC increases the heart rate to four beats during the high pleural pressure interval (instead of three) and increases the shift of blood out of the lung to 4 ml (instead of 3 ml). Thus, the CPRC produces a net shift of 2 ml out of the lung during a single breathing-cycle (within 5 sec). Although the effect within a single breathing-cycle is small, it is accumulative, and within one minute it produces a net outflow of 24 ml out of the lung, when the respiratory rate is 12 bpm as in FIG. 3, or 120 ml within only 10 minutes. It is important to note that under normal condition there are only about 500 ml of blood within the lung, and accumulated effect within 10 ml is huge (theoretically can decrease the lung blood volume by 24%). The effect of CPRC may diminish with time as the lung blood pool may decrease. However, lung congestion, an increase in the respiratory effort and a deeper modulation of the CPRC (larger difference between the inspiratory and expiratory heart rate) intensify the effects of the CPRC in a cooperative mode, and cooperatively assist in alleviating the hemodynamic and lung congestions.

Additionally it is noted that:

(1) One simple implementation of the suggested 'cardiopulmonary reverse cycling therapy' includes:

A. Quantification of the severity of the respiratory effort, a surrogate of dyspnea, by measuring the amplitude of the respiratory wave within the chest cage.

B. Setting the appropriate threshold by the long-term central control subsystem, and segmentation of the breathing cycles to time segments below the threshold (deep negative phase) and time segments above the threshold (close to zero pleural pressure). C. Placing a single pacing electrode within the right atrium (if the patient does not suffer from atrial arrhythmia or any kind of atrioventricular block).

D. Increase of the pacing rate when the pleural pressure is close to zero (end expiration and early inspiration, as shown in FIG. 4), without the need to artificially suppress the normal sinus node. The pacing is control by the real-time central control subsystem E. Providing adaptive control of the pacing rate. The pacing is modulated according to the severity of the respiratory effort. The long-term central subsystem determines provides this adaptive control of the pacing based on the acquired sensing.

A single cable can include the needed sensing (A) and pacing (C).

(2) Recent studies have shown that lung congestion develops over a prolonged period of time in heart failure patients. The pulmonary capillary wedge pressure and the pulmonary artery pressure increase slowly and gradually over a time period of 2 to 3 weeks, before there is a need for more aggressive treatment or hospitalization. Thus, although the suggested method causes a small shift of fluid from the lung back to the periphery, it can work slowly and persistently over a long time interval of days, and thus can prevent the gradual development of lung congestion.

(3) Both an increase in the respiratory effort amplitude and prolongation of the inspiratory phase from 20-25% of the breathing cycle toward 50% of the cycle promote lung congestion. The first increases the shift of blood into the lung at each heart beat and the latter increases the number of heart beats during each inspiratory phase. Hemodynamic and lung congestion increase the respiratory effort. The suggested 'cardiopulmonary reverse cycling therapy' breaks the 'cardiopulmonary vicious cycle' and is expected to decrease the hemodynamic congestion and the associated respiratory effort and the duration of inspiration. Therefore, the cardiopulmonary reverse cycling therapy may be modulated by the respiratory effort.

(4) The device has an insignificant effect on cardiac output, although it has a significant effect on lung congestion. It has a small effect on the cardiac output since it has a small effect in the heart rate. Despite this negligible effect on the cardiac output there is a large accumulative effect on the lung blood pool and a large shift of blood from the lung back into the periphery.

(5) Additional advantage of the invention is it protective effect from atrial fibrillation in heart failure patients. Hemodynamic and lung congestions are associated with huge respiratory effort. The respiratory effort and the associated huge decrease in the intrapleural pressure (to −20 mmHg and more, as was observed in heart failure patients) significantly increase the transmural atrial pressure and lead to atrial dilatation. This mechanism can facilitate the deterioration of atrial function and leads to atrial dilatation and the development of atrial fibrillation. Thus, prevention of hemodynamic congestion and the decrease in the transmural atrial pressure can prevent the development of atrial fibrillation.

Applications of the invention include, without limitation, treatment of heart failure patients, including all heart failure types. The invention aims to decrease the probability of gradual development of hemodynamic or lung congestion. The invention may provide precise diagnosis of the severity of the decompensation, based on the assessment of the severity of respiratory effort and the hemodynamic congestion. Moreover, it provides the immediate and the proportional appropriate treatment for the prevention of further deterioration and the return toward normal condition. Dyspnea is the most cardinal symptom of heart failure, and the technology directly targets this symptom.

It is important to note that:

(1) There is no effective treatment for heart failure with preserve ejection fraction, and this technology can alleviate the symptom of these patients.

(2) The invention provides immediate diagnosis and real-time treatment, something which does not exist in the prior art.

(3) The invention has minor effects on cardiac output and can even increase the cardiac output, unlike diuretic therapies that can cause over dehydration with reduction in the cardiac output. Unlike the regular prior-art diuretic therapy that has no control on the balance between the peripheral and the pulmonary blood pools, the invention can provide this important control on the shift of blood between the peripheral and the pulmonary blood pools.

The invention claimed is:

1. A method for treatment of cardiac problems, comprising:

performing electrical modulation of a cardiac pacing of a patient in response to measured pleural pressures, by increasing a number of heart beats during a first time segment in which there is a first pleural pressure relative to a number of heart beats in a second time segments in which there is a second pleural pressure, the first pleural pressure being higher than the second pleural pressure.

2. The method according to claim 1, wherein the modulation of the cardiac pacing is effective to remove fluids from a lung of the patient, and to reduce pressures within pulmonary vessels of the patient and to reduce a sensation of dyspnea.

3. The method according to claim 1, wherein the modulation of the cardiac pacing reduces resistance to blood flow within pulmonary circulation of the patient and reduces the respiratory effort and thereby alleviates both right and left ventricle workloads.

4. The method according to claim 1, wherein the modulation of the cardiac pacing is determined by a severity of a respiratory effort of the patient and wherein the modulation of the cardiac pacing is based upon feedback from sensors within a pleural space or/and intrathoracic vessels and/or heart chamber or/and a body surface of the patient, said sensors being used to sense the pleural pressures or to record and measure respiratory waves, and wherein the severity of the respiratory effort is defined as peak to peak amplitude of the respiratory waves, and the severity of respiratory effort is used as the feedback to modulate the cardiac pacing.

5. The method according to claim 1, wherein the modulation of the cardiac pacing further comprises using a long-term central control system, with memory and communication units, that records past history of heart rate, respiratory dynamics and hemodynamic indices.

6. The method according to claim 5, wherein the modulation of the cardiac pacing further comprises performing said cardiac pacing in accordance with a respiratory rate (RR) interval of elicited pacing, based on past history of electrocardiogram (ECG) recordings and/or respiratory indices as recorded in said memory.

7. The method according to claim 1, wherein the modulation of the cardiac pacing further comprises using a long-term central control system, with a central processing unit that senses changes in hemodynamic congestion or hemodynamic pressure, respiratory effort and/or heart rates.

8. The method according to claim 1, wherein the modulation of the cardiac pacing further comprises segmenting respiratory cycles into intervals in which a first interval has a first pleural pressure, called a relatively high pleural pressure, and a second interval which has a second pleural pressure, called a relatively low pleural pressure, wherein said first pleural pressure is higher than said second pleural pressure.

9. The method according to claim 8, wherein the modulation of the cardiac pacing further comprises increasing the number of heart beats during time intervals with the relatively high pleural pressure or by decreasing the number of heart beats during time segments with the relatively low pleural pressure.

10. The method according to claim 8, further comprising identifying in real time a beginning of each high pleural pressure interval and computing a pacing time based on identifying a last heartbeat, a number of pacing beats provided recently and a required number of pacing beats that should be added per minutes (NpM).

11. The method according to claim 1, wherein the modulation of the cardiac pacing further comprises modulating a given cardiac pacing that comprises sinus node pacing and the modulation comprises suppressing said sinus node pacing.

12. The method according to claim 1, wherein the modulation of the cardiac pacing further comprises using feedback from sensors that assess respiratory effort level, to control the modulation of the cardiac pacing, wherein said control of the modulation comprises determining a number of pacing beats that should be added per minutes (NpM), that are added during the high pleural pressure intervals, and wherein a depth of the modulation (NpM) increases with severity of the monitored respiratory effort.

13. The method according to claim 1, further comprises using a real time control unit and an output power unit that executes the cardiac pacing.

14. The method according to claim 1, wherein the modulation of the cardiac pacing is carried out by pacing electrodes placed within at least one cardiac chamber.

15. The method according to claim 1, wherein said high-first pleural pressure is closer to zero than said relatively lower-second pleural pressure.

16. The method according to claim 1, wherein the modulation of the cardiac pacing is controlled by an implanted controller.

17. The method according to claim 16, wherein a depth or an amplitude or a duration or a time period of the modulation of the cardiac pacing is determined by a severity of a respiratory effort and lung congestion of the patient.

18. The method according to claim 1, wherein the modulation of the cardiac pacing is controlled by an extracorporeal controller or by an implanted controller which is controlled by the extracorporeal controller.

19. The method according to claim 18, wherein a depth or an amplitude or a duration or a time period of the modulation of the cardiac pacing is determined by a severity of a respiratory effort and lung congestion of the patient.

20. The method according to claim 1, wherein the modulation of the cardiac pacing starts before expiration of the patient ends and ends after inspiration of the patient begins.

21. The method according to claim 1, wherein said increasing the number of heart beats during the first time segment relative to the number of heart beats in the second time segment comprises adding heart beats in said first time segment or reducing heart beats in said second segment.

* * * * *